United States Patent [19]

Sundberg et al.

[11] Patent Number: 4,752,572
[45] Date of Patent: Jun. 21, 1988

[54] LIPID VESICLES CONTAINING LABELED SPECIES AND THEIR ANALYTICAL USES

[75] Inventors: Michael W. Sundberg, Penfield; David F. O'Brien; Susan J. Danielson, both of Rochester, all of N.Y.

[73] Assignee: Eastman Kodak Company, Rochester, N.Y.

[21] Appl. No.: 771,548

[22] Filed: Aug. 30, 1985

[51] Int. Cl.[4] .................. G01N 33/53; G01N 33/535
[52] U.S. Cl. .......................................... 435/7; 264/4.1; 428/402.2; 435/805; 435/810; 436/808; 436/810; 436/829
[58] Field of Search ................. 436/829, 808, 810; 424/417, 450; 435/7, 805, 810; 264/4.1; 428/402.2

[56] References Cited

U.S. PATENT DOCUMENTS

| 3,850,578 | 11/1974 | McConnell | 23/230 B |
|---|---|---|---|
| 3,887,698 | 6/1975 | McConnell et al. | 424/12 |
| 3,896,217 | 7/1975 | Johnson | 424/1 |
| 3,993,754 | 11/1976 | Rahman | 436/450 X |
| 4,084,967 | 4/1978 | O'Brien | 96/29 R |
| 4,193,983 | 3/1980 | Ullman et al. | 424/12 |
| 4,235,792 | 11/1980 | Hsia et al. | 260/403 |
| 4,235,871 | 11/1980 | Papahadjopoulos et al. | 424/19 |
| 4,255,411 | 3/1981 | Lim et al. | 424/1 |
| 4,310,505 | 1/1982 | Baldeschwieler et al. | 424/1 |
| 4,314,021 | 2/1982 | O'Brien et al. | 430/270 |
| 4,342,739 | 8/1982 | Kakimi et al. | 424/1 |
| 4,342,826 | 8/1982 | Cole | 435/7 |
| 4,343,895 | 8/1982 | Sugaar | 435/6 |
| 4,356,256 | 10/1982 | O'Brien et al. | 430/332 |
| 4,372,745 | 2/1983 | Mandle et al. | 436/537 |
| 4,429,008 | 1/1984 | Martins et al. | 428/402.2 |
| 4,517,303 | 5/1985 | Freytag | 436/829 X |
| 4,666,830 | 5/1987 | Wagner | 436/829 X |

FOREIGN PATENT DOCUMENTS

| 0014530 | 8/1980 | European Pat. Off. . |
|---|---|---|
| 0090735 | 10/1983 | European Pat. Off. . |
| 56-79255 | 6/1981 | Japan . |
| 57-19661 | 2/1982 | Japan . |
| WO83/01571 | 5/1983 | World Int. Prop. O. . |
| 2079936 | 1/1982 | United Kingdom . |
| 2079937 | 1/1982 | United Kingdom . |

OTHER PUBLICATIONS

Patel, H. M., Febs Letters, 62(1), 60-63 (Feb. 1976).

Primary Examiner—Sidney Marantz
Attorney, Agent, or Firm—J. Lanny Tucker

[57] ABSTRACT

Vesicles comprising a matrix of lipid membranes prepared from lipid materials are useful in biomedical studies and immunoassays. A labeled species is encapsulated within the vesicles and released when the vesicles are lysed with a surface active agent. The outer surface of the vesicles is essentially free of the labeled species. Immunoassays can be carried out in solution or with a dry analytical element.

18 Claims, 1 Drawing Sheet

LIPID VESICLES CONTAINING LABELED SPECIES AND THEIR ANALYTICAL USES

FIELD OF THE INVENTION

This invention relates to encapsulated labeled species and their use in biomedical studies and clinical chemistry determinations. These encapsulated species are particularly useful in competitive binding assays, e.g. immunoassays, to determine a specific binding ligand, e.g. an antigen.

BACKGROUND OF THE INVENTION

In the fields of medicine and clinical chemistry, determinations are required of analytes (identified herein as ligands) that are present in biological fluids in very low concentrations, e.g. proteins, enzymes, cofactors, hormones, narcotics, steroids, therapeutic drugs, antigens, antibodies, etc. Several techniques have been developed for the determination of these low level analytes. One useful technique is a competitive binding immunoassay. In a competitive binding immunoassay, a labeled ligand (identified herein as a ligand analog) is placed in competition with unlabeled ligand for a fixed amount of a common binding material (identified herein as a receptor). Unknown concentration of the ligand can be determined from the measured signal from either the bound or free ligand analog.

In such determinations, it is often desirable to keep the ligand analog in close proximity to the receptor without premature reaction of the receptor and ligand analog.

A procedure used in most immunoassays to avoid the problem of premature binding of ligand analog and receptor is to add the ligand analog to the reaction medium at the same time or after the ligand is added in the test sample. This procedure, however, complicates the assay because it requires additional steps which makes operator error more likely.

Immunoassays can be carried out in either solution or with dry analytical elements. Such elements can be either single layer filter strips or more complicated multilayer test slides. Use of any dry element in an assay requires some means for preventing premature binding of ligand analog with the receptor which may already be in the element. In some instances, the ligand analog is positioned in a zone or layer separate from that containing the receptor. However, this arrangement complicates the manufacturing process because it requires additional zones or layers to be constructed.

Synthetic membranes are well known in the art. One type of membrane can be prepared by dispersing lipids in water. These membranes are also known as liposomes. A vesicle is a liposome having a single lipid bilayer forming a spherical shell.

Vesicles have been used to encapsulate labeled species. For example, U.S. Pat. No. 4,372,745 (issued Feb. 8, 1983 to Mandle et al) describes a heterogeneous immunoassay in which phospholipid vesicles are used to encapsulate fluorescers. The vesicles containing the fluorescer are conjugated to an immunological species which is outside the vesicle. A nonionic surfactant is used to lyse the vesicles during the assay.

However, in this immunoassay, premature binding of ligand analog with receptor can still occur. The ligand portion of the analog is outside the vesicle rendering the ligand available for binding prior to vesicle lysis. In the Mandle et al assay, the vesicle is merely used as a means of attaching the fluorescer to the ligand. This technique is useful where the fluorescer can not be conjugated to the ligand directly.

Similarly, in U.S. Pat. Nos. 3,850,578 (issued Nov. 26, 1974 to McConnell) and 3,887,698 (issued June 3, 1975 to McConnell et al), vesicles are used to encapsulate stable free radicals useful in an immunoassay. These vesicles have at least one determinant or epitopic (i.e. antigentic) site on the outer membrane surface which will complex with antibody. Like the Mandle et al label, the McConnell label is subject to premature binding because the ligand portion of the label is available to the receptor prior to the assay.

A number of other references describe the use of vesicles containing various labels and having a ligand bound to the outer vesicle membrane either directly or through a linking group, including U.K. Pat. Nos. 2,079,936 and 2,079,937 (both published Jan. 27, 1982), U.S. Pat. No. 4,342,826 (issued Aug. 3, 1982 to Cole) and European Patent Application No. 14,530 (published Aug. 20, 1980). However, all of the materials described in these references are subject to premature binding between the ligand attached to the outside of the vesicle and the receptor.

It would be desirable to have a means for preventing the premature binding of labeled species and corresponding receptor when the two materials are in the same environment.

SUMMARY OF THE INVENTION

We have found a means to prevent the premature binding of receptor and ligand analog when the two materials are present in the same environment. The materials of our invention can be used to advantage in biomedical studies and clinical determinations, such as immunoassays where the ligand is present in low concentration. This important advantage is achieved by encapsulating the complete ligand analog inside vesicles which can be lysed when binding is desired. There are essentially no ligand molecules or binding sites on the outer surface of the vesicles, unlike the vesicles of the prior art.

Therefore, in accordance with this invention, a composition comprises vesicles which comprise lipid membranes with a labeled physiologically active species encapsulated therein, and have an outer surface which is essentially free of the labeled species. In a preferred embodiment, the active species is an immunologically active ligand and the outer surface of the vesicles is essentially free of both the ligand and its receptor.

The present invention also provides a dry analytical element for the determination of an immunologically active ligand. This element comprises an absorbent carrier material containing the vesicle composition described above. In a preferred embodiment, the element comprises a support having thereon a porous spreading zone.

Further, this invention comprises a method for the determination of an immunologically active ligand in a liquid. The method comprises the steps of:

A. in the presence of a receptor for the ligand, contacting a sample of the liquid with the vesicle composition described above, B. lysing the vesicles, and C. determining the labeled analog in bound or unbound form.

DETAILED DESCRIPTION OF THE INVENTION

Figure 1:
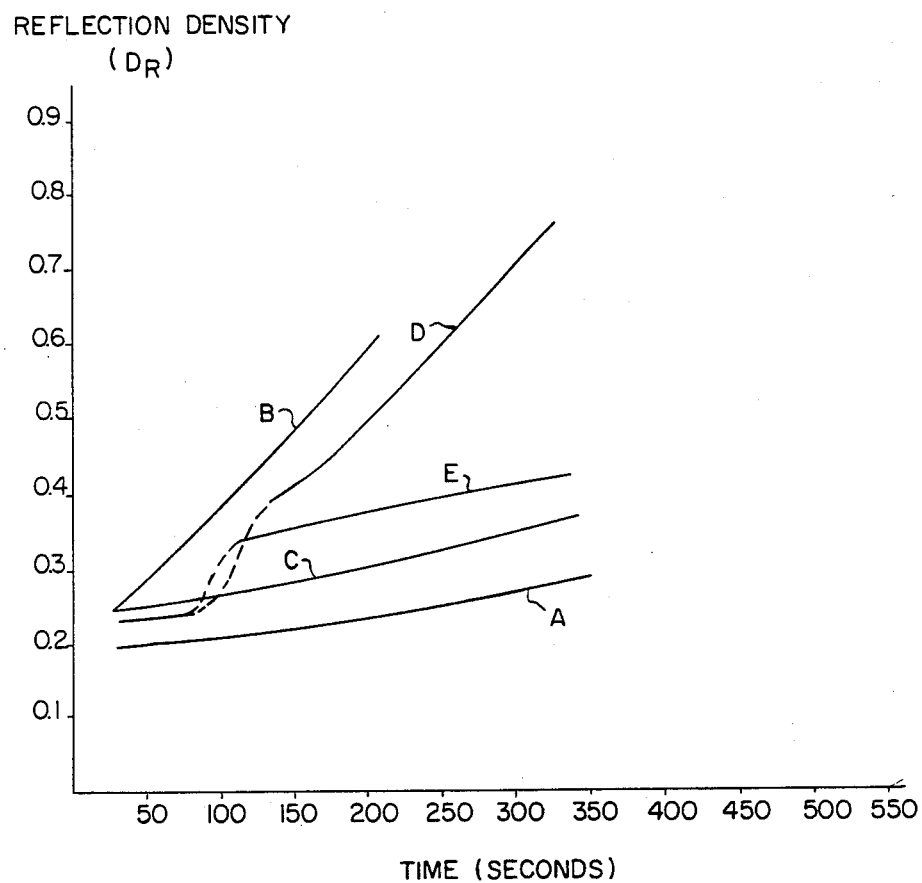
FIG. 1 is a graphical plot of reflection density ($D_R$) measured at 670 nm versus time in seconds for a number of determinations of phenobarbital as described in Example 2 below.

The composition of this invention can be used in a variety of biomedical studies and clinical determinations. For example, this composition can be used to label cells or physiologically active species including proteins (e.g. albumin, IgG, IgM, etc.), nucleic acids (e.g. DNA), enzymes and their substrates (e.g. creatine kinase, lactate dehydrogenase, creatine, lactate, etc.), cofactors, viruses, leukocytes, growth factors, antigens, haptens including therapeutic and narcotic drugs (e.g. theophylline, digoxin, phenobarbital, digitoxin, morphine, barbiturates, lidocaine, gentamicin, etc.), antibodies (e.g. microsomal antibody, antibodies to hepatitis and allergens), metabolites (e.g. adenosine-5'-monophosphate), hormones and hormone receptors, (e.g. thyroxine, insulin, estriol, chorionic gonadotropin, liothyronine, peptide hormones, etc.), plant lectins, toxins, vitamins (e.g. biotin, vitamin $B_{12}$, folic acid, vitamin E, ascorbic acid, etc.), natural and synthetic steroids (e.g. cortisol, aldosterone, progesterone, etc.), and other pharmacological agents and their receptors, and other binding substances enabling the detection of such substances.

The compositions of this invention are particularly useful for determining immunologically active ligands in immunoassays. Such assays utilize three components: the species to be determined, i.e. the ligand, a specific binding partner for the ligand, i.e. a receptor, and a labeled species which can be a labeled ligand or labeled receptor. The immunoassay can be either homogeneous or heterogeneous as those terms are known in the art. In the following discussion and presentation of examples, reference will be made primarily to these preferred embodiments, but it is to be understood that the scope of the invention is inclusive of any other competitive binding assay.

Useful labeling moieties in the practice of this invention include fluorescers, chemiluminescent compounds, radioisotopes, enzymes, cofactors and enzyme modulators. Enzymes, e.g. glucose oxidase, peroxidase, alkaline phosphatase and β-galactosidase, are the preferred labeling moieties. The techniques and materials used to bind the ligand to the labeling moiety either directly or through linking groups are well known in the art. Generally, the ligand is covalently bound to the labeling moiety. A representative procedure for preparing a ligand analog is provided below just before the examples.

The vesicles useful in the practice of this invention are well known in the art. They are saclike structures, e.g. liposomes, which are arranged to form a bilayer membrane. The molecules used in forming the membranes are amphiphatic. The bilayer structure has hydrophilic moieties arrayed on the outside of the membrane and hydrophobic moieties arrayed on the inside. An adequate description of lipid membranes and lipids which are useful herein can be found in U.S. Pat. No. 4,356,256 (issued Oct. 26, 1982 to O'Brien et al) and the references noted therein in Column 4.

Especially useful lipid membranes are selected from the group consisting of:

Phospholipids, e.g. phosphatidylcholine, phosphatidylethanolamine, phosphatidylserine, phosphatidylglycerol, phosphatidylinositol and phosphatidic acid, sphingolipids, such as sphingomyelin and ceramide phosphorylethanolamine, glycolipids, such as cerebrosides, phytoglycolipids, gangliosides, glycerides, phosphonolipids, such as ceramide-2-aminoethylphosphonic acid and phosphonoglycerides, sterols, such as cholesterol, lanosterol, ergosterol and β-sitosterol, and fatty acids, such as palmitic acid and stearic acid.

The vesicles useful in this invention are preferably prepared from phospholipids represented by the following structure:

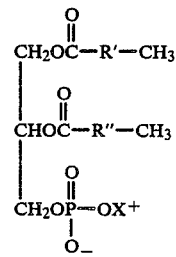

wherein R' and R" are independently divalent substituted or unsubstituted aliphatic groups (unsaturated or saturated), preferably containing at least 10 carbon atoms, and more preferably from 14 to 22 carbon atoms. Representative examples of R' and R" groups include alkylene (e.g. octylene, decylene, 2-methyldecylene, tetradecylene, hexadecylene, octadecylene, 2,6,10,14-tetramethyltetradecylene and the like), alkenylene (e.g. 3-decenylene, 8-hexadecenylene and the like), alkyleneoxy-alkylene (e.g. octyl-ene-oxy-hexylene and the like), and alkyldienylenes (e.g. 8,11-hexadecadiene, 1,3-hexadecadiene and the like).

In the above structure, X is an alkylene quaternary ammonium cation wherein the alkylene portion is substituted or unsubstituted and has from 1 to 6 carbon atoms and preferably from 1 to 3 carbon atoms. Representative X groups include 2-trimethylammonioethyl, ammonioethyl, 2-carboxy-2-ammonioethyl and the like. Further examples of phospholipids are described in *Methods in Membrane Biology*, by Korn, Vol. 1, Plenum Press, New York, 1974, pp. 55–60.

The compositions of this invention comprising vesicles containing a labeled species, e.g. a ligand analog, can be prepared by any of a number of known procedures including:

the reverse phase evaporation method described by Szoka et al, *Proc. Nat'l. Acad. Sci., USA*, 75, pp. 4194–4198, 1978, and in U.S. Pat. No. 4,235,871 (issued Nov. 25, 1980 to Papahadjopoulos et al), the ether injection method described by Deamer et al, *Biochim. Biophys. Acta*, 443, pp. 629–634, 1976, the Freon injection method described by Cafiso et al, *Biochim. Biophys. Acta*, 649, pp. 129–132, 1981, detergent dialysis of lipids in octyl glucoside described by Mimms et al, *Biochemistry*, 20, pp. 833–838, 1981, calcium-induced fusion of the negatively charged phospholipids described by Paphadjopoulos et al, *Biochim. Biophys. Acta*, 394, pp. 483-491. 1975, and a modification of reverse phase evaporation method described by Kim et al, *Biochim. Biophys. Acta*, 646, pp. 1-9, 1981.

A preferred method is the reverse phase evaporation method noted above. A representative preparation of a vesicle composition is shown in Example 1 below. In general, this method is carried out by preparing the lipid membranes, incorporating the labeled species therein and purifying the lipid membranes.

Either the ligand or the receptor alone can be incorporated into vesicles, or each can be incorporated into separate vesicles for use in the same composition or analytical element.

The molar ratio of ligand analog to lipid in the vesicles can vary widely, but is generally from about 1:500 to about 1:50,000. The preferred molar ratio is from about 1:1000 to about 1:10,000.

The size of the vesicles formed can vary, but generally is between about 0.05 to about 5 $\mu$m as estimated by negative stain electron microscopy. A preferred size range is from about 0.1 to about 1 $\mu$m.

The composition and method of this invention are adaptable to both solution and dry element studies or assays. In a solution assay, the test sample is physically contacted and mixed with the vesicle composition and appropriate receptor in a suitable container (e.g. test tube, petrie dish, beaker, cuvette, etc.). The vesicles are lysed in an appropriate manner to release the ligand analog. The resulting solution can be incubated, if desired, for a time (e.g. up to several hours) at a temperature of up to about 45° C. (generally at 37° C.) to hasten the formation of a complex of the receptor with both the ligand and the ligand analog. The sample is then evaluated by measuring the amount of detectable signal (e.g. fluorescence or dye formation) resulting from the binding reactions. Separation of bound and unbound ligand can be carried out using conventional separation techniques.

The vesicles can be lysed in any suitable manner, including changing the pH, hydrolysis, photolysis, ultrasonic agitation, or any combination of these and other techniques. A preferred technique is to contact the vesicles with a surfactant.

Surfactants which are useful in the practice of the present invention include any which will effectively lyse substantially all of the vesicles, thereby releasing the ligand analog from within. A simple test can be performed to determine whether or not a particular surfactant is so useful. A mixture of 1 to 10 g/l surfactant and about 0.1 g/l vesicles are mixed in a suitable container and the amount of lysing is measured by the observed decrease in turbidity in the mixture. At least about 99% of the vesicles should be lysed.

Particularly useful surfactants can also be identified as those which have a critical micelle concentration of at least about 0.1 mmolar. Critical micelle concentration is a well known surfactant parameter which is the concentration above which the surfactant molecules aggregate to form micelles. Representative lysing surfactants include nonionic materials, such as those commercially available under the trademark TRITON from Rohm and Haas (Philadelphia, Pa., U.S.A.), TWEEN available from ICI Americas (Wilmington, Del., U.S.A.), and octyl glucoside available from Sigma Chemical Co. (St. Louis, Mo., U.S.A.), and anionic materials, such as sodium cholate and sodium dodecyl sulfate available from Eastman Kodak Co. (Rochester, N.Y., U.S.A.).

The amount of surfactant used in solution with the vesicle in an assay or biomedical study is an amount sufficient to lyse substantially all of the vesicles. This amount will vary depending upon the vesicle concentration and surfactant used, but is generally at least about 0.1 g/l, and preferably from about 0.5 to about 5 g/l. The amount of the vesicle composition used in an assay is dependent upon the ligand to be determined and can be determined by one of ordinary skill in the art. The amount of receptor used is similarly determined. Other materials, e.g. buffers, activators, cofactors, reagents, catalysts, color couplers, etc. can be included in known amounts if desired.

The analytical composition of this invention can be provided, along with a lysing surfactant and the receptor, as part of a diagnostic kit for either dry or solution assay. For solution assays, the kit components can be supplied in bottled or otherwise packaged solutions sufficient in size for one or more assays. Other optional reagents and addenda can also be supplied in the kit along with suitable assay utensils or containers and directions for performing the assay. A dry analytical element, described below, can be supplied as part of the kit.

A sandwich assay can also be used in the practice of this invention. For example, this assay involves the use of two different antibodies. A first antibody can be immobilized, on the sides of a test tube, for example, for a solution assay, or in a spreading layer of an element for a dry assay. A second antibody (with an appropriate label, e.g. an enzyme label) is then incorporated in the vesicles and added to the tube for a solution assay, or added to or incorporated in an analytical element (described below). The test sample is then added and the assay conducted as described.

The method of this invention can also be practiced with a dry analytical element which can be composed of an absorbent carrier material, i.e. thin sheet of self-supporting absorbent or bibulous material, such as a filter paper or strip, which contains the vesicle composition of this invention. Such elements can also contain in any suitable location, a receptor for a specific binding assay immobilized in a suitable manner. Such elements are known in the art as test strips, diagnostic elements, dip sticks, diagnostic agents and the like.

When employed in dry analytical elements, the composition of this invention can be incorporated into a suitable carrier material by imbibition or impregnation, or coated in the absorbent material on a suitable support. Useful carrier materials are insoluble and maintain their structural integrity when exposed to water or physiological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

Preferably, the dry analytical elements of this invention have at least one porous spreading zone as the absorbent carrier material. This zone can be self-supporting (i.e. composed of a material rigid enough to maintain its integrity), but preferably it is carried on a suitable nonporous support. Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (e.g. reflection, transmission or fluorescence spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in U.S. Pat. No. 4,430,436 (issued Feb. 7, 1984 to Koyama et al) and Japanese Patent Publication No. 57(1982)-101760 (published June 24, 1982). It is desirable that the spreading zone be isotropically porous, meaning that the porosity is the same in each direction in the zone as created by interconnected spaces or pores between particles, fibers, polymeric strands, etc.

The elements can have one or more reagent zones, spreading zones, registration zones, mordant zones, radiation-blocking or filter zones, subbing zones, barrier zones, buffer zones, etc. The zones are generally in fluid contact with each other meaning that fluids, reagents and reaction products can pass between superposed or adjacent regions or zones. Preferably, the zones are separately coated superposed layers, although the zones can be portions of a single layer.

The analytical composition of this invention can be incorporated in any zone of the element. Alternatively, it can be added to the test sample which is subsequently applied to the element. The receptor corresponding to the ligand to be determined can also be in any zone of the element in an immobilized form.

In the elements of this invention, the coverage of vesicles can be varied widely, but it is generally up to about $10^3$, and preferably from about $10^{-2}$ to about $10^2$ g/m$^2$. The receptor is generally present in a coverage of from about $10^{-6}$ to about 1 g/m$^2$. The lysing surfactant can be incorporated in the element if it is kept isolated from the vesicles prior to the assay. For example, it could be placed in one zone while the vesicles are in another zone to be released only when the test liquid and element are contacted. When present, the surfactant coverage is at least about 0.01, and preferably from about 0.05 to about 0.5, g/m$^2$. A variety of other desirable, but optional, reagents and addenda can be present in the element in amounts known to one skilled in the art. Such materials include interactive reagents, non-lysing surfactants, buffers, binders, pigments, activators, etc.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, determination of a ligand is made by taking the element from a supply roll, chip packet or other source and physically contacting it with a sample (e.g. 1-100 μl) of the liquid to be tested in the presence of the receptor. Such contact can be accomplished in any suitable manner, e.g. dipping or immersing the element into the sample or, preferably, by spotting the element by hand or machine with a drop of the sample with a suitable dispensing means.

For example, the assay of this invention can be carried out according to the teaching of copending U.S. Ser. No. 757,111 of Frickey et al, filed July 19, 1985 and entitled HETEROGENEOUS IMMUNOASSAY UTILIZING HORIZONTAL SEPARATION IN AN ANALYTICAL ELEMENT.

After sample application, the element is exposed to any conditioning, such as incubation, heating or the like, that may be desirable to quicken or otherwise facilitate obtaining any test result. Determination of the ligand is achieved by measuring the detectable signal from either the bound (i.e. complexed) or unbound (i.e. noncomplexed) labeled ligand analog.

The separation of bound and free labeled ligand analog can be accomplished using any of a number of procedures, including those described in U.S. Pat. Nos. 3,817,837 (issued June 18, 1974 to Rubenstein et al) and 3,654,090 (issued Apr. 4, 1972 to Schuurs et al), and in the Frickey et al application noted above. Also useful are radial wash techniques described, for example, in U.S. Pat. No. 4,517,288 (issued May 14, 1985 to Geigel et al).

In one embodiment of this invention, an enzyme-labeled antigen conjugate, such as phenobarbital-glucose, oxidase, is encapsulated in phospholipid vesicles. The conjugate can be released by lysing the vesicles with TRITON X-100 surfactant. The vesicles can be applied to the element prior to application of the surfactant and test sample.

In another embodiment of the invention, the vesicles are incorporated into the element at the time of manufacture using known manufacturing techniques and materials.

In these embodiments, the released enzyme-labeled antigen provides glucose oxidase which, in the presence of oxygen, converts glucose to gluconic acid and hydrogen peroxide. Hydrogen peroxide, in the presence of peroxidase, then can cause the conversion of a leuco dye to a detectable dye, or cause the reaction of a color coupler with an oxidizable compound to form a detectable dye. The rate of dye formation can be correlated to the amount of enzyme label which is bound to phenobarbital antibody. This can then be correlated to the amount of phenobarbital in the test sample. Useful reagents and amounts of each, e.g. leuco dyes, are well known in the art.

In the following enzyme label-antigen preparation and examples illustrating the practice of this invention, the materials used were obtained as follows:

rabbit antiphenobarbital antisera from Kallestad Laboratories (Chaska, Minn., U.S.A.), glucose oxidase, cholesterol and egg phosphatidylcholine from Sigma Chemical Co. (St. Louis, Mo., U.S.A.), sodium 5-ethyl-5-phenylbarbiturate from Mallinkrodt Chemical Co. (St. Louis, Mo., U.S.A.), TRITON X-100 surfactant from Rohm & Haas (Philadelphia, Pa., U.S.A.), ZONYL FSN and ALKANOL XC surfactants from DuPont Co. (Wilmington, Del., U.S.A.), peroxidase from Miles Laboratories (Elkhart, Ind., U.S.A.), and the remainder from Eastman Kodak Co. (Rochester, N.Y., U.S.A.) or prepared using known starting materials and synthetic procedures.

A phenobarbital-glucose oxidase conjugate was prepared in the following manner for use in the examples below.

Step 1: The Preparation of 1-(4-Ethoxycarbonylbutyl)-5-Ethyl-5-Phenylbarbituric Acid:

Sodium 5-ethyl-5-phenylbarbitate (5.0 g, 0.019 molar) was suspended in 50 ml of dry N,N-dimethylformamide. To the stirred suspension, ethyl-5-bromovalerate (4.6 g, 0.022 molar) was added dropwise. The reaction mixture was gently heated to 40° C. for 10 minutes then stirred at room temperature for 16 hours. After addition of 1 g of potassium iodide, the reaction mixture was stirred an additional 6 hours.

A stream of filtered nitrogen was passed over the reaction mixture until a semi-solid product was obtained which was dissolved in 250 ml of dichloromethane. The resulting solution was washed with 100 ml of distilled water, 100 ml of 2.5% sodium bicarbonate solution, 50 ml of 2.5% sodium bicarbonate, 50 ml of distilled water, and then dried over sodium sulfate. Evaporation of the solvent yielded 5.6 g of solid product which was shown to be a mixture of mono and diesters of 5-ethyl-5-phenylbarbituric acid. A sample (1.4 g) of the ester mixture was dissolved in 4 ml of chloroform and chromatographed on a silica gel column (300 g, 2.5 cm × 36 cm) using chloroform-acetonitrile (95/5) as the eluting solvent. Diester eluted in the first 600 ml and monoester at 950–1450 ml of eluting solvent. The pure monoester weighed 0.45 g.

Step 2: The Preparation of 1-(4-Carboxybutyl)-5-Ethyl-5-Phenylbarbituric Acid:

The ester from Step 1 (0.77 g) is dissolved in a mixture of 16.3 ml of concentrated hydrochloric acid, 32.5 ml of tetrahydrofuran, and 6.5 ml of water. The hydrolysis mixture was stirred overnight at room temperature, then the tetrahydrofuran was removed under reduced pressure. To the reaction mixture, 50 ml of saturated sodium chloride solution was added. This mixture was extracted four times with 50 ml portions of dichloromethane. The dichloromethane extract was then extracted three times with 50 ml portions of saturated sodium bicarbonate solution. The combined bicarbonate extracts were carefully acidified at ice-water bath temperature to pH 2–3 with concentrated hydrochloric acid. A white solid precipitated.

The acidified mixture was extracted three times with 50 ml portions of dichloromethane. The dichloromethane extract was washed with 50 ml of chilled water and dried over sodium sulfate. Evaporation of the dichloromethane yielded 0.9 g of sticky solid. The solid was dissolved in 2 ml of ether. Petroleum ether was added dropwise until slight cloudiness was induced. The solution was kept in the freezer overnight. The crystalline product was collected and dried overnight at reduced pressure. The product weighed 0.63 g.

Analysis calculated for $C_{17}H_{20}N_2O_5$: C, 61.4; H, 6.1; N, 8.4. Found: C, 61.3; H, 6.2; N, 8.2.

Step 3: The Preparation of Phenobarbital-Glucose Oxidase Conjugate:

Glucose oxidase (5 mg/ml) was dialyzed against 2 liters of 0.05 molar potassium phosphate buffer (pH=7) for 24 hours. The buffer was changed two times. The dialyzed glucose oxidase (20 ml, $6.25 \times 10^{-7}$ mole) was diluted to 50 ml with distilled water, and the pH was adjusted to 8.5 with dilute NaOH.

1-(4-Carboxybutyl)-5-ethyl-5-phenylbarbituric acid (41.5 mg, $1.25 \times 10^{-4}$ mole) was dissolved in 4 ml dry dioxane. Tributylamine (29.8 µl, $1.25 \times 10^{-4}$ mole) was added, and the solution was cooled to 15° C. Isobutylchloroformate (16 µl, $1.25 \times 10^{-4}$ mole) was added, the reaction mixture was stirred for 20 minutes at 15° C. This product was added dropwise to the glucose oxidase solution, and the reaction was stirred at room temperature for 30 minutes while the pH was maintained at 8.5.

The reaction mixture was then dialyzed against 2 liters of 0.05 molar $KH_2PO_4$ (pH=7) for two days. The buffer was changed 2–3 times. The reaction mixture was concentrated on a commercial Minicon B-15 sample concentrator available from Amicon Corp. (Danvers, Mass., U.S.A.) and was then chromatographed on a Bio-Gel P-6 column 200–400 mesh) available from Bio-Rad Labs (Richmond, Calif., U.S.A.) equilibrated in 0.05 molar $KH_2PO_4$ (pH=7). The yield was 75%.

Protein Concentration=6.41 mg/ml
Activity=1197 I.U./ml, 187 I.U./mg
Ligand:Enzyme Ratio=20:1

As used in the context of this disclosure, I.U. represents the International Unit for enzyme activity defined as one I.U. being the amount of enzyme activity required to catalyze the conversion of 1 micromole of substrate per minute under standard pH and temperature conditions for the enzyme.

EXAMPLE 1

Preparation of Analytical Composition

This example illustrates the preparation of a vesicle composition, its purification and the determination of the amount of ligand analog incorporated into the vesicles.

A mixture of egg phosphatidylcholine (69 mg, 90 mmoles), cholesterol (26 mg, 67 mmoles) and palmitic acid (5.6 mg, 22 mmoles) in diethyl ether and chloroform was dried to a thin film in a flask attached to a rotary evaporator. The lipids were redissolved in 10 ml of diethyl ether and dried to a thin film twice in succession to remove all chloroform. The lipid mixture was then dissolved in 9 ml of diethyl ether and combined with 3 ml of a solution of the phenobarbital-glucose oxidase prepared above (1 mg/ml) in phosphate-buffered saline solution (0.01 molar phosphate, 0.15 molar Cl, pH 7.3) that was diluted 1 to 10 with water. The two-phase mixture was sonicated for 3 to 5 minutes in a cold ultrasonic bath to yield a stable emulsion of lipid, ether, and water. The ether was then removed slowly by rotary evaporation using high speed rotation in a reduced-pressure nitrogen atmosphere to form a thick white gel of lipid and aqueous liquid. Buffer solution (12 ml) was then added to the sample and rotary evaporation repeated to insure the complete removal of the residual ether. A white aqueous dispersion of vesicles containing labeled phenobartital was obtained.

The aqueous vesicle dispersion was thoroughly mixed. A sample (0.5 ml) was removed, and the remaining volume measured. The mixture was then centrifuged for 20 minutes at 20,000 rpm at 8° C. in a commercial Sorvall RC2-B centrifuge. The supernate was decanted and retained, and the pellet was resuspended by vortex mixing in a volume of buffered solution equal to its original volume. The lipid vesicles were then recentrifuged and the supernatant discarded. This wash process was repeated four times.

The final pellet was resuspended in the original volume of buffered solution by vortex mixing and assayed for enzyme activity in the presence and absence of 1% TRITON X-100 surfactant. For comparison, the crude vesicle preparation was assayed under the same conditions. The resulting data are shown in the Table below.

A reagent solution for measuring enzyme activity was prepared by combining 50 ml of a potassium phosphate solution (0.05 molar, pH 7), 1.0 ml of an o-dianisidine solution (3.33 mg/ml), and 0.5 ml of a horseradish peroxidase solution (2.5 mg/ml). The reagent solution was stable on ice for at least one day. To 0.90 ml of the reagent solution was added 0.10 ml of a substrate solution (18 g of a glucose 100 ml, 1 mole/liter) in a spectrophotometer cuvette and the combined solutions allowed to incubate for 5-7 minutes at 37° C.

The solution to be assayed was diluted with buffered solution to an approximate final activity of 50-100 I.U./ml and the reaction initiated by adding 0.050 ml of the diluted sample to the incubating cuvette. The cuvette was then inverted 2 or 3 times, and the change in absorbance with time at 430 nm was recorded using a commercial Cary 219 spectrophotometer. The activity in the original solution (I.U./ml) was computed by multiplying the change in absorbance per minute by 1.93 times the total dilution factor of the sample (before introduction into the cuvette).

Typical assay results are listed below. Results are expressed as I.U./mg of total enzyme.

| Solution | Glucose Oxidase Activity (I.U./mg) | |
| --- | --- | --- |
| | no Triton ™ X-100 | with Triton ™ X-100 |
| Crude Vesicle Composition | 147 | 236 |
| Purified Vesicle Composition | 1 | 16 |

These data indicate that the purified composition contains essentially all ligand analog within the vesicles and none outside the vesicles, and the vesicles can be lysed to release ligand analog.

EXAMPLE 2

Use of an Analytical Element to Determine Phenobarbital

An analytical element was prepared having the following format and components:

| | | |
| --- | --- | --- |
| Spreading Layer | Rabbit antiphenobarbital antisera immobilized | 30–130 g/m² |
| | on polystyrene beads | |
| | KH₂PO₄ buffer (pH 7) | 0.06–0.3 g/m² |
| | Poly(butyl acrylate-co-styrene-co-2-acryl-amido-2-methylpropane sulfonic acid, sodium salt) adhesive | 1–6 g/m² |
| | ZONYL FSN surfactant | 0.2–1.5 g/m² |
| Registration Layer | Gelatin (hardened) | 2–20 g/m² |
| | 2-(3,5-Dimethyl-4-hydroxyphenyl)-4,5-bis(4-dimethylaminophenyl)imidazole leuco dye | 0.1–0.6 g/m² |
| | 2,4-Di-n-amylphenol | 0.5–3.5 g/m² |
| | Glucose | 1–4 g/m² |
| | Dimedone | 0.1–0.4 g/m² |
| | ALKANOL XC Surfactant | 0.02–0.2 g/m² |
| | Peroxidase | 5,000–50,000 I.U./m² |
| | Poly(ethylene terephthalate) Support | |

The following solutions were prepared and applied to a finite area of the spreading layer of the multilayer element shown above. Immobilized ligand-receptor complex was formed in the finite area and unbound ligand migrated horizontally away from the finite area, as described in U.S. Ser. No. 757,111 noted above. The rate of dye formation from the bound ligand analog in the finite area was measured at 670 nm. The results are shown in FIG. 1.

Solution A

A 5 µl aliquot of the purified vesicle composition described above was applied to the above element and the rate of dye formation was measured. Curve A in FIG. 1 was obtained. The rate of dye formation was minimal indicating that although ligand analog and antibody are present in the same environment, essentially no binding takes place because ligand analog is contained in the vesicles.

Solution B

The vesicle composition was premixed with a TRITON X-100 surfactant solution (final concentration 1%), and then a 5 µl aliquot was applied to the element and the rate of dye formation was measured. Curve B was obtained. The increased rate indicates that the ligand analog was released from the vesicles and bound by antibody.

Solution C

The vesicle composition containing 1 mmolar phenobarbital was premixed with a TRITON X-100 surfactant solution (final concentration 1%) and then a 5 µl aliquot was applied to the element. The rate of dye formation was measured. Curve C was obtained. Phenobarbital effectively competed with the released conjugate for the antibody binding sites. Although the ligand analog was released from the vesicles, as in Solution B, very little analog was bound by antibody.

Solution D

A 5 µl aliquot of the vesicle composition was applied to the element. After 75 seconds, the first spot was overspotted with TRITON X-100 surfactant solution (1%). Curve D was obtained. The increase in rate after the addition of TRITON X-100 surfactant solution is the same as with Curve B, and indicates that the ligand analog was released from the vesicles and bound to the immobilized antibody.

Solution E

A 5 μl aliquot of the vesicle composition was applied to the element. After 75 seconds, a solution containing TRITON X-100 (1%) and 1 mmolar phenobarbital was applied to the same area of the element. Curve E was obtained. The rate is similar to that shown in Curve C. Phenobarbital effectively competed with the released conjugate for antibody binding sites when added with TRITON X-100 surfactant to the element after addition of the vesicles.

These data indicate that when receptor and labeled ligand analog are present in the same environment essentially no premature binding takes place (Solution and Curve A). The binding reaction does occur, however, when the vesicles are lysed (Solutions and Curves B and D). Thus, the method of this invention can be used with this element to determine phenobarbital.

EXAMPLE 3

The Determination of Phenobarbital in an Analytical Element

An analytical element, prepared as shown in Example 2, was used for the determination of phenobarbital. Solutions of the vesicles containing phenobarbital glucose oxidase conjugate in sodium phosphate buffer (0.05 molar, pH 7), prepared as described in Example 1, were spotted onto the element using 5 μl samples. Then, solutions containing varying concentrations of phenobarbital (1–128 μg/ml) and TRITON X-100 surfactant (1% by weight) in buffer were spotted onto the same area of the element using 5 μl samples. The reflection density of dye formed from immobilized ligand analog in the center of the spotted area was measured at 670 nm at 37° C. over 3–5 minutes. The Williams-Clapper transform (F. C. Williams and F. C. Clapper, *J. Optical Soc. Am.*, 43:595, 1953) was used to obtain transmission density ($D_T$) values. The resulting data are shown in the following Table.

TABLE I

| Phenobarbital (Phe) Assa | |
|---|---|
| Phe Concentration (μg/ml) | Rate ($D_T$/Min) |
| 1 | 0.069 |
| 2.5 | 0.069 |
| 5 | 0.063 |
| 8 | 0.061 |
| 20 | 0.058 |
| 40 | 0.057 |
| 80 | 0.055 |
| 128 | 0.052 |

The invention has been described in detail with particular reference to preferred embodiments thereof, but it will be understood that variations and modifications can be effected within the spirit and scope of the invention.

We claim:

1. An analytical composition for determining an immunologically active ligand comprising vesicles, said vesicles consisting essentially of lipid membranes with a labeled analog of said ligand encapsulated therein, and having an outer surface which is essentially free of said ligand and a receptor therefor.

2. The composition of claim 1 wherein said labeled ligand is an enzyme-labeled ligand.

3. The composition of claim 1 wherein said labeled ligand is a labeled antigen.

4. The composition of claim 1 wherein said lipid membranes are prepared from materials selected from the group consisting of phospholipids, sphingolipids, glycolipids, phosphonolipids, sterols and fatty acids.

5. The composition of claim 4 wherein said membrane material is a phospholipid represented by the structure:

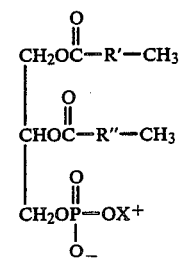

wherein R' and R" are independently divalent aliphatic groups, and X is an alkylene quaternary ammonium cation.

6. A dry analytical element for the determination of an immunologically active ligand, said element comprising an absorbent carrier material containing a composition comprising vesicles,
said vesicles comprising lipid membranes with a labeled analog of said ligand encapsulated therein, and having an outer surface which is essentially free of said ligand and a receptor therefor.

7. The element of claim 6 wherein said lipid membranes are prepared from materials selected from the group consisting of phospholipids, sphingolipids, glycolipids, phosphonolipids, sterols and fatty acids.

8. A dry analytical element for the determination of an immunologically active ligand comprising
a support having thereon a porous spreading zone, and
a composition comprising vesicles, said vesicles comprising phospholipid membranes represented by the structure:

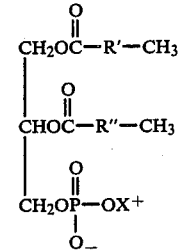

wherein R' and R" are independently divalent aliphatic groups, and X is an alkylene quaternary ammonium cation,
said vesicles having a labeled analog of said ligand encapsulated therein, and an outer surface essentially free of said ligand and a receptor therefor.

9. The element of claim 8 comprising a receptor for said ligand.

10. A dry multilayer analytical element for the determination of an antigen comprising a support having thereon, in order and in fluid contact, a registration layer comprising a colorimetric indicator composition and an enzyme substrate, an isotropically porous spreading layer comprising immobilized antibody for said antigen and vesicles comprising phospholipid membranes represented by the structure:

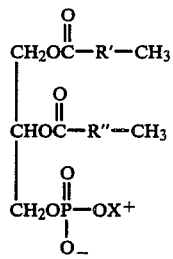

wherein R' and R" are independently alkylene groups, and X is an alkylene quaternary ammonium cation, said vesicles having said antigen labeled with an enzyme encapsulated therein, and an outer surface essentially free of said antigen and said antibody.

11. A method for the determination of an immunologically active ligand in a liquid, said method comprising the steps of:
   A. in the presence of a receptor for said ligand, contacting a sample of said liquid with an analytical composition comprising vesicles,
   said vesicles comprising lipid membranes with a labeled analog of said ligand encapsulated therein, and having an outer surface essentially free of said ligand and receptor,
   B. lysing said vesicles, and
   C. determining said labeled analog in bound or unbound form.

12. The method of claim 11 wherein said vesicles are lysed with a surfactant having a critical micelle concentration of at least about 0.1 mmolar.

13. The method of claim 11 wherein said lipid membranes are prepared from materials selected from the group consisting of phospholipids, sphingolipids, glycolipids, phosphonolipids, sterols and fatty acids.

14. The method of claim 13 wherein said membrane material is a phospholipid represented by the structure:

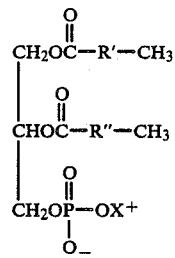

wherein R' and R" are independently divalent aliphatic groups, and X is an alkylene quaternary ammonium cation.

15. The method of claim 11 wherein said analytical composition is contained in a dry analytical element.

16. The method of claim 15 wherein said element contains a receptor for said ligand.

17. A method for the determination of an antigen in a biological fluid, said method comprising the steps of:
   A. in the presence of an antibody for said antigen, contacting a sample of said fluid with an analytical composition comprising vesicles,
   said vesicles comprising lipid membranes prepared from a phospholipid represented by the structure:

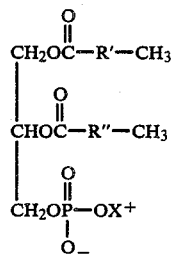

wherein R' and R" are independently alkylene groups, and X is an alkylene quaternary ammonium cation,
   said vesicles having said antigen labeled with an enzyme encapsulated therein, and an outer surface essentially free of said antigen and said antibody,
   B. lysing said vesicles with a surfactant having a critical micelle concentration of at least about 0.1 mmolar, and
   C. determining said enzyme-labeled antigen in bound or unbound form.

18. A diagnostic test kit for the determination of an immunologically active ligand, said kit comprising
   (i) a receptor for said ligand,
   (ii) an analytical composition comprising vesicles, said vesicles comprising lipid membranes with a labeled analog of said ligand encapsulated therein, and having an outer surface which is essentially free of said ligand and said receptor, and
   (iii) a surfactant capable of lysing said vesicles having a critical micelle concentration of at least about 0.1 mmolar.

* * * * *